United States Patent
Yanagisawa et al.

(10) Patent No.: US 9,420,782 B2
(45) Date of Patent: Aug. 23, 2016

(54) PESTICIDAL COMPOSITION IN THE FORM OF AQUEOUS EMULSION

(71) Applicant: Sumitomo Chemical Company, Limited, Tokyo (JP)

(72) Inventors: Kazuyuki Yanagisawa, Takarazuka (JP); Motofumi Mizutani, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/411,159

(22) PCT Filed: Jun. 20, 2013

(86) PCT No.: PCT/JP2013/067586
§ 371 (c)(1),
(2) Date: Dec. 24, 2014

(87) PCT Pub. No.: WO2014/003083
PCT Pub. Date: Jan. 3, 2014

(65) Prior Publication Data
US 2015/0140053 A1 May 21, 2015

(30) Foreign Application Priority Data

Jun. 26, 2012 (JP) .................. 2012-142762

(51) Int. Cl.
*A01N 25/04* (2006.01)
*A01N 37/36* (2006.01)
*A01N 25/22* (2006.01)

(52) U.S. Cl.
CPC .............. *A01N 25/04* (2013.01); *A01N 25/22* (2013.01); *A01N 37/36* (2013.01)

(58) Field of Classification Search
None
See application file for complete search history.

(56) References Cited

U.S. PATENT DOCUMENTS

| | | |
|---|---|---|
| 2003/0134910 A1 | 7/2003 | Rose et al. |
| 2006/0129021 A1 | 6/2006 | Tanedani |
| 2008/0125480 A1 | 5/2008 | Pedersen et al. |
| 2011/0197318 A1 | 8/2011 | Takaishi et al. |
| 2012/0270732 A1 | 10/2012 | Takaishi et al. |

FOREIGN PATENT DOCUMENTS

| | | |
|---|---|---|
| EP | 1283009 A1 | 2/2003 |
| EP | 2245929 A1 | 11/2010 |
| EP | 2245930 A1 | 11/2010 |
| EP | 2245931 A1 | 11/2010 |
| JP | S59-39807 A | 3/1984 |
| JP | 2009173596 A | 8/2009 |
| JP | 2010222256 A | 10/2010 |
| WO | 9315605 A2 | 8/1993 |
| WO | 0200023 A1 | 1/2002 |
| WO | 2006069580 A1 | 7/2006 |
| WO | 2008032328 A2 | 3/2008 |
| WO | 2008047569 A2 | 4/2008 |
| WO | 2008047570 A2 | 4/2008 |
| WO | 2009112836 A2 | 9/2009 |
| WO | 2011028286 A1 | 3/2011 |
| WO | 2012121413 A1 | 9/2012 |

OTHER PUBLICATIONS

International Search Report issued Aug. 6, 2013 in International Application No. PCT/JP2013/067586.
Extended Search Report issued Feb. 19, 2016 in EP Application No. 13809629.2.
Examination Report issued Mar. 2, 2016 in AU Application No. 2013281754.

*Primary Examiner* — Abigail Fisher
*Assistant Examiner* — Frank Choi
(74) *Attorney, Agent, or Firm* — Panitch Schwarze Belisario & Nadel LLP

(57) ABSTRACT

A pesticidal composition in the form of an aqueous emulsion contains: (a) an agriculturally active ingredient in which a retention rate is 50% or more after irradiation with xenon light (290 nm cutoff) at an intensity of 0.68 W/m$^2$ at 340 nm for 8 hours, and a retention rate is 40% or more and 60% or less after irradiation for 56 hours; (b) a hydrophobic organic solvent; (c) a water-soluble polymer dispersing agent; and (d) water; wherein liquid droplets in which the agriculturally active ingredient is suspended or dissolved in the hydrophobic organic solvent are emulsified in an aqueous continuous phase. A weight ratio of the agriculturally active ingredient to the hydrophobic organic solvent is from 5:95 to 70:30. With this pesticidal composition, it is possible to inhibit photodegradation of the agriculturally active ingredient.

4 Claims, No Drawings

PESTICIDAL COMPOSITION IN THE FORM OF AQUEOUS EMULSION

CROSS-REFERENCE TO RELATED APPLICATION

This application is a Section 371 of International Application No. PCT/JP2013/067586, filed Jun. 20, 2013, which was published in the English language on Jan. 3, 2014, under International Publication No. WO 2014/003083 A1, and the disclosure of which is incorporated herein by reference.

TECHNICAL FIELD

The present invention relates to a pesticidal composition in the form of an aqueous emulsion in which photodegradation of an agriculturally active ingredient has been inhibited.

BACKGROUND ART

Various studies have hitherto been made for the purpose of inhibiting photodegradation of agriculturally active ingredients which are unstable against light. There have been known technologies in which stabilizers such as an ultraviolet absorber are added (see, for example, Patent Document 1). There is also known a pesticidal composition in the form of an aqueous emulsion, which contains a specific water-soluble polymer as a stabilizer in an aqueous continuous phase (see, for example, Patent Document 2).

PRIOR ART DOCUMENT

Patent Document

[Patent Document 1]: JP 59-39807 A
[Patent Document 2]: US 2003/0,134,910 A

DISCLOSURE OF INVENTION

Problems to be Solved by the Invention

An object of the present invention is to provide a new pesticidal composition in the form of an aqueous emulsion in which photodegradation of an agriculturally active ingredient has been inhibited.

Means for Solving the Problems

The present inventors have intensively studied so as to find a pesticidal composition in the form of an aqueous emulsion in which photodegradation of an agriculturally active ingredient has been inhibited, and found that, in a pesticidal composition in the form of an aqueous emulsion, comprising:
(a) an agriculturally active ingredient in which a retention rate is 50% or more after irradiation with xenon light (290 nm cutoff) at an intensity of 0.68 W/m² at 340 nm for 8 hours, and a retention rate is 40% or more and 60% or less after irradiation for 56 hours (hereinafter sometimes referred to as a component a);
(b) a hydrophobic organic solvent (hereinafter sometimes referred to as a component b);
(c) a water-soluble polymer dispersing agent (hereinafter sometimes referred to as a component c); and
(d) water (hereinafter sometimes referred to as a component d);
wherein liquid droplets in which the component a is suspended or dissolved in the component b are emulsified in an aqueous continuous phase, when a weight ratio of the component a to the component b is within a specific range, it is possible to inhibit photodegradation of the component a.

The present invention includes the followings:
[1] A pesticidal composition in the form of an aqueous emulsion, comprising:
(a) an agriculturally active ingredient in which a retention rate is 50% or more after irradiation with xenon light (290 nm cutoff) at an intensity of 0.68 W/m² at 340 nm for 8 hours, and a retention rate is 40% or more and 60% or less after irradiation for 56 hours;
(b) a hydrophobic organic solvent;
(c) a water-soluble polymer dispersing agent; and
(d) water;
wherein liquid droplets in which the agriculturally active ingredient is suspended or dissolved in the hydrophobic organic solvent are emulsified in an aqueous continuous phase, and also a weight ratio of the agriculturally active ingredient to the hydrophobic organic solvent is from 5:95 to 70:30;
[2] The pesticidal composition in the form of an aqueous emulsion according to [1], wherein the liquid droplets have an average particle diameter of 5 to 60 μm;
[3] The pesticidal composition in the form of an aqueous emulsion according to [1] or [2], wherein the agriculturally active ingredient is an agriculturally active ingredient which is solid at normal temperature;
[4] The pesticidal composition in the form of an aqueous emulsion according to any one of [1] to [3], wherein the hydrophobic organic solvent(s) is/are one or more hydrophobic organic solvent(s) selected from the group consisting of esters, ketones, aromatic hydrocarbons, and paraffins; and
[5] The pesticidal composition in the form of an aqueous emulsion according to any one of [1] to [4], wherein the water-soluble polymer dispersing agent(s) is/are one or more water-soluble polymer dispersing agent(s) selected from the group consisting of a vinyl-based polymer, polysaccharides, and derivatives thereof.

Effects of the Invention

According to the present invention, it is possible to inhibit photodegradation of an agriculturally active ingredient.

MODE FOR CARRYING OUT INVENTION

The pesticidal composition in the form of an aqueous emulsion of the present invention (hereinafter sometimes referred to as a composition of the present invention) is a pesticidal composition in the form of an aqueous emulsion (emulsion pesticidal composition) containing an agriculturally active ingredient which is unstable against light, such as the component a, and is a pesticidal composition which can effectively inhibit photodegradation of the agriculturally active ingredient.

As used herein, xenon light means a light source in which a gas filled in a tube is xenon. Usually, xenon light means uniquely the same spectrum. Xenon light (290 nm cutoff) means xenon light having a wavelength within a range of 290 nm or more, and xenon light passed through a borosilicate filter corresponds to this.

A method for the calculation of a retention rate of the agriculturally active ingredient defined above is more specifically as follows. First, 250 mg of the agriculturally active ingredient is dissolved in 50 mL of a solvent such as acetone, which can sufficiently dissolve the agriculturally active ingredient and also has high volatility, and 1 mL of the solution is added to a glass petri dish having a diameter of 6 cm using a one-mark pipette, spread entirely over the petri dish, and then air-dried at room temperature. The petri dish is covered with a lid made of quartz glass and then set in a weathering tester (manufactured by Q-Lab Corporation under the trade name of Q-SUN Xenon Accelerated Weathering Tester, Model Xe-3) equipped with a borosilicate filter (manufactured by Q-Lab Corporation under the trade name of Daylight-BB Optical Filter) attached thereto. After irradiation with xenon light under the conditions of an intensity at 340 nm of 0.68 W/m$^2$ and a temperature of 35° C. (35° C. as measured by an insulated black panel thermometer) for a predetermined time, the amount of the agriculturally active ingredient remaining on the petri dish is determined by a known determination method such as high-performance liquid chromatography. It is possible to determine a retention rate by calculating as the weight percentage relative to 5 mg of the agriculturally active ingredient used above.

The above agriculturally active ingredient used in the composition of the present invention may be any of an insecticidally active component, a fungicidally active component, and a herbicidally active component, and is not particularly limited. It is preferred to use an agriculturally active ingredient which is solid at normal temperature (25° C.). The agriculturally active ingredient includes, for example, 2-[(2,5-dimethylphenoxy)methyl]-α-methoxy-N-methyl-benzeneacetamide (CAS Registry No. 173662-97-0) in which a retention rate is 93.1% after irradiation with xenon light (290 nm cutoff) at an intensity of 0.68 W/m$^2$ at 340 nm for 8 hours, and a retention rate is 50.3% after irradiation for 56 hours according to the method for calculation above-mentioned.

The composition of the present invention usually contains a component a in the total amount of 0.5 to 25% by weight, and preferably 2.5 to 15% by weight.

In the composition of the present invention, a component b means an organic solvent which is liquid at normal temperature (25° C.) and is immiscible in water. Specifically, an organic solvent having water solubility of 20% by weight or less at 25° C. is used. Examples of the hydrophobic organic solvent include hydrophobic organic solvents such as vegetable oils, esters, ketones, aromatic hydrocarbons, and paraffins, for example, the following hydrophobic organic solvents:

Vegetable oils: rapeseed oil, soybean oil, linseed oil, corn oil, and olive oil;

Esters: diisobutyl adipate, diisodecyl adipate, dialkyl phthalate (didecyl phthalate, etc.), octyl oleate, lauryl oleate, octyldodecyl oleate, and isopropyl myristate;

Ketones: methyl isobutyl ketone, heptanone, octanone, nonanone, cyclohexanone, and acetophenone; and Aromatic hydrocarbons: toluene, xylene, phenylxylylethane, 1-phenyl-1-ethylphenylethane, methylnaphthalene, dimethylnaphthalene, triisopropylbiphenyl, and dimethylisopropylnaphthalene.

In the present invention, commercially available aromatic hydrocarbon solvents can be used as aromatic hydrocarbons. Examples of the commercially available aromatic hydrocarbon solvents include Hisol SAS-296 (mixture of 1-phenyl-1-xylylethane and 1-phenyl-1-ethylphenylethane, trade name of JX Nippon Oil & Energy Corporation), Hisol SAS-LH (trade name of JX Nippon Oil & Energy Corporation), CACTUS SOLVENT HP-MN (methylnaphthalene 80%, trade name of JX Nippon Oil & Energy Corporation), CACTUS SOLVENT HP-DMN (dimethylnaphthalene of 80%, trade name of JX Nippon Oil & Energy Corporation), CACTUS SOLVENT P-180 (mixture of methylnaphthalene and dimethylnaphthalene, trade name of JX Nippon Oil & Energy Corporation), CACTUS SOLVENT P-200 (mixture of methylnaphthalene and dimethylnaphthalene, trade name of JX Nippon Oil & Energy Corporation), CACTUS SOLVENT P-220 (mixture of methylnaphthalene and dimethylnaphthalene, trade name of JX Nippon Oil & Energy Corporation), CACTUS SOLVENT PAD-1 (dimethylmonoisopropylnaphthalene, trade name of JX Nippon Oil & Energy Corporation), Solvesso 100 (aromatic hydrocarbon, trade name of ExxonMobil Chemical Ltd.), Solvesso 150 (aromatic hydrocarbon, trade name of ExxonMobil Chemical Ltd.), Solvesso 200 (aromatic hydrocarbon, trade name of ExxonMobil Chemical Ltd.), Solvesso 150ND (aromatic hydrocarbon, trade name of ExxonMobil Chemical Ltd.), Solvesso 200ND (aromatic hydrocarbon, trade name of ExxonMobil Chemical Ltd.), Ruetasolv BP 4302 (manufactured by RKS GmbH), NIKANOL (trade name of Fudow Company Limited.), SWASOL 100 (toluene, trade name of Maruzen Petrochemical CO, LTD.), and SWASOL 200 (xylene, trade name of Maruzen Petrochemical CO, LTD.).

Paraffins: normal paraffin, isoparaffin, cycloparaffin, and liquid paraffin

In the present invention, commercially available paraffin solvents can be used as paraffins. Examples of the commercially available paraffin solvents include NORPAR 13 (normal paraffin, the trade name of ExxonMobil Chemical Ltd.), NORPAR 15 (normal paraffin, the trade name of ExxonMobil Chemical Ltd.), ISOPAR E (isoparaffin, trade name of ExxonMobil Chemical Ltd.), ISOPAR G (isoparaffin, trade name of ExxonMobil Chemical Ltd.), ISOPAR L (isoparaffin, trade name of ExxonMobil Chemical Ltd.), ISOPAR H (isoparaffin, trade name of ExxonMobil Chemical Ltd.), ISOPAR M (isoparaffin, trade name of ExxonMobil Chemical Ltd.), MORESCO-WHITE P-40 (liquid paraffin, trade name of MORESCO Corporation), MORESCO-WHITE P-70 (liquid paraffin, trade name of MORESCO Corporation), MORESCO-WHITE P-200 (liquid paraffin, trade name of MORESCO Corporation), EXXSOL D110 (mixed solvent of paraffin and cycloparaffin, trade name of ExxonMobil Chemical Ltd.), EXXSOL D130 (mixed solvent of paraffin and cycloparaffin, trade name of ExxonMobil Chemical Ltd.), and EXXSOL D160 (mixed solvent of paraffin and cycloparaffin, trade name of ExxonMobil Chemical Ltd.).

There is no particular limitation on the component b used in the composition of the present invention. Of these, one or more hydrophobic organic solvent(s) selected from the group consisting of esters, ketones, aromatic hydrocarbons, and paraffins is/are preferably used.

In the composition of the present invention, a weight ratio of the component a to the component b is from 5:95 to 70:30, preferably from 15:85 to 70:30, and more preferably from 30:70 to 70:30. The composition of the present invention usually contains the component b in the total amount of 5 to 40% by weight, and preferably 10 to 25% by weight.

There is no particular limitation on a component c used in the composition of the present invention, and one or more water-soluble polymer dispersing agent(s) selected from the group consisting of a vinyl-based polymer, polysaccharides, and derivatives thereof is/are preferably used.

Examples of the water-soluble vinyl-based polymer include polyvinyl alcohol, polyvinylpyrrolidone, vinyl acetate copolymer, and sodium polyacrylate. Examples of the water-soluble polysaccharides and derivatives thereof include gum arabic, xanthan gum, rhamsan gum, locust bean gum, guar gum, carrageenan, welan gum, alginic acid, alginate, gum tragacanth, methyl cellulose, ethyl cellulose, sodium carboxymethyl cellulose, hydroxyethyl cellulose, and hydroxypropyl cellulose. In the present invention, the vinyl-based polymer means a polymer obtained by addition polymerization of a monomer having a vinyl group (—CH=CH$_2$), and polysaccharides mean saccharides which are hydrolyzed to form two or more molecules of monosaccharides.

The composition of the present invention usually contains the component c in the total amount of 1 to 10% by weight, and preferably 1 to 5% by weight.

There is no particular limitation on a component d used in the composition of the present invention, and it is possible to use water which is used in a conventional pesticidal composition in the form of an aqueous emulsion (emulsion pesticidal composition), such as tap water, well water, and deionized water, and deionized water is preferably used.

The composition of the present invention usually contains the component d in the amount of 40 to 93% by weight, and preferably 45 to 90% by weight. Substantially, the component c is dissolved in the component d.

It is preferred that the composition of the present invention further contains one or more UV protectants. Examples of the UV protectants include benzophenone-based ultraviolet absorbers such as 2,4-dihydroxybenzophenone, 2-hydroxy-4-methoxybenzophenone, and 2-hydroxy-4-n-octylbenzophenone; benzotriazole-based ultraviolet absorbers such as 2-(2-hydroxy-5-methylphenyl)benzotriazole, 2-[2-hydroxy-3-(3,4,5,6-tetrahydrophthalimide-methyl)-5-methylphenyl]benzotriazole, 2-(3-tert-butyl-2-hydroxy-5-methylphenyl)-5-chlorobenzotriazole, 2-(2-hydroxy-5-tert-octylphenyl)benztriazole, and 2-(2-hydroxy-3,5-di-tert-pentylphenyl)benzotriazole; benzoate-based ultraviolet absorbers such as 2,4-di-tert-butylphenyl 3,5-di-tert-butyl-4-hydroxybenzoate; hydroxyphenyltriazine-based ultraviolet absorber such as 2-(2-hydroxy-4-[1-octyloxycarbonylethoxy]phenyl)-4,6-bis(4-phenylphenyl)-1,3,5-triazine; photostabilizers such as non-sulfonated lignin (for example, manufactured by MeadWestvaco Corporation under the trade name of INDULIN AT) and a hindered amine-based photostabilizer (HALS); and inorganic UV shielding agents such as titanium oxide.

Substantially, the UV protectant (hereinafter sometimes referred to as a component e) is suspended or dissolved in the component b. There is no particular limitation on the component e used in the composition of the present invention, and it is preferred to use a component e, which is miscible in the component b, from the viewpoint of emulsion stability of liquid droplets as the component b which contains the component e in the composition in the form of an aqueous emulsion.

When the composition of the present invention contains the component e, the total content is usually from 0.1 to 15% by weight, and preferably from 0.5 to 10% by weight.

The composition of the present invention may further contain pesticide auxiliary agents used in a conventional pesticidal composition in the form of an aqueous emulsion. Examples of the pesticide auxiliary agents include surfactants, thickeners, defoamers, preservatives, antifreezing agents, pH adjustors and the like.

Examples of the surfactants include nonionic surfactants, cationic surfactants, anionic surfactants, and amphoteric surfactants. Examples of nonionic surfactants include polyoxyethylene alkyl ether, polyoxyethylene alkyl aryl ether, polyoxyethylene lanolin alcohol, polyoxyethylene alkyl phenol formalin condensate, polyoxyethylene sorbitan fatty acid ester, polyoxyethylene glyceryl monofatty acid ester, polyoxypropylene glycol monofatty acid ester, polyoxyethylene sorbitol fatty acid ester, polyoxyethylene castor oil derivative, polyoxyethylene fatty acid ester, higher fatty acid glycerol ester, sorbitan fatty acid ester, sucrose fatty acid ester, polyoxyethylene polyoxypropylene block polymer, polyoxyethylene fatty acid amide, alkylol amide, polyoxyethylenealkylamine, and polyoxyethylene alkanediol. Examples of cationic surfactants include alkylamine hydrochlorides such as dodecylamine hydrochloride; alkyl quaternary ammonium salts such as dodecyltrimethyl ammonium salt, alkyldimethylbenzyl ammonium salt, alkylpyridinium salt, alkylisoquinolinium salt, and dialkylmorpholinium salt; benzethonium chloride, and polyalkyl vinyl pyridinium salt. Examples of anionic surfactants include fatty acid sodium such as sodium palmitate; sodium ether carboxylate such as sodium polyoxyethylene lauryl ether carboxylate; amino acid condensates of higher fatty acid, such as sodium lauroyl sarcosine and sodium N-lauroyl glutamate; higher fatty acid ester sulfonates such as higher alkyl sulfonate and lauric acid ester sulfonic acid salt; dialkyl sulfosuccinates such as dioctyl sulfosuccinate; higher fatty acid amide sulfonates such as oleic acid amide sulfonic acid; alkyl aryl sulfonates such as sodium dodecylbenzene sulfonate and diisopropyl naphthalene sulfonate; higher alcohol sulfuric acid ester salts such as formalin condensate of alkyl aryl sulfonate and pentadecane-2-sulfate; polyoxyethylene alkyl phosphates such as dipolyoxyethylene dodecyl ether phosphate; styrene-maleic acid copolymer; and lignin sulfonate.

Examples of amphoteric surfactants include N-laurylalanine, N,N,N-trimethylaminopropionic acid, N,N,N-trihydroxyethylaminopropionic acid, N-hexyl-N,N-dimethylaminoacetic acid, 1-(2-carboxyethyl)pyridinium betaine, and lecithin.

When the composition of the present invention contains the surfactant, the total content is usually from 0.1 to 20% by weight, and preferably from 0.5 to 10% by weight.

Examples of the thickener include natural polysaccharides such as xanthan gum, rhamsan gum, locust bean gum, guar gum, carrageenan, welan gum, alginic acid, alginate, and gum tragacanth; mineral matter powders such as aluminum silicate, magnesium aluminum silicate, smectite, bentonite, hectorite, synthetic hydrated silicic acid, and dry silica; and alumina sol. It is possible to use, as these thickeners, commercially available products as they are. Examples of commercially available products include KELZAN S (trade name of CP Kelco, Inc.) as xanthan gum, VEEGUM Granules (trade name of Vanderbilt Company, Inc.) as aluminum silicate, an Aerosil 200 (trade name of Evonik Degussa Corporation) as dry silica.

When the composition of the present invention contains the thickener, the total content is usually from 0.01 to 10% by weight, and preferably from 0.1 to 5% by weight.

Examples of the defoamer include silicone-based defoamers such as ANTIFOAM C EMULSION (trade name of Dow Corning Toray Co., Ltd.), ANTIFOAM CE (trade name of Dow Corning Toray Co., Ltd.), TSA730 (trade name of MOMENTIVE PERFORMANCE MATERIALS JAPAN LLC), TSA731 (trade name of MOMENTIVE PERFORMANCE MATERIALS JAPAN LLC), TSA732 (trade name of MOMENTIVE PERFORMANCE MATERIALS JAPAN LLC), and YMA6509 (trade name of MOMENTIVE PER- FORMANCE MATERIALS JAPAN LLC); and fluorine-based defoamers such as Fluowet PL80 (trade name of Clariant GmbH).

When the composition of the present invention contains the defoamer, the total content is usually from 0.01 to 3% by weight, and preferably from 0.05 to 1% by weight.

Examples of the preservative include p-hydroxybenzoic acid ester, salicylic acid derivative, proxel (1,2-benzisothiazolin-3-one), and isothiazolin-3-one derivative (for example, BIOHOPE L (trade name of KI Chemical Industry Co., Ltd.)).

When the composition of the present invention contains the preservative, the total content is usually from 0.01 to 5% by weight, and preferably from 0.05 to 3% by weight.

Examples of the antifreezing agent include water-soluble glycols such as ethylene glycol and propylene glycol.

When the composition of the present invention contains the antifreezing agent, the total content is usually from 0.5 to 30% by weight, and preferably from 1 to 20% by weight.

Examples of the pH adjustor include citric acid monohydrate, sorbic acid, potassium sorbate, disodium hydrogen phosphate, dipotassium hydrogen phosphate, and sodium hydroxide.

When the composition of the present invention contains the pH adjustor, the total content is usually from 0.01 to 5% by weight, and preferably from 0.5 to 3% by weight.

A method for producing a composition of the present invention (hereinafter sometimes referred to as a present production method) will be described, but the present production method is not limited only to the following methods.

The present production method includes the following first and second steps.

The first step of the present production method is the step of suspending or dissolving a component a in a component b to prepare a suspension or a solution of the component a.

The component a is suspended or dissolved in the component b.

When the component a is a component a which is solid at normal temperature (25° C.) (hereinafter sometimes referred to as a solid component a), it is possible to take the form of a suspension (hereinafter sometimes referred to as a present suspension a) depending on solubility of the solid component a in the component b and a weight ratio of the solid component a to the component b. The present suspension a can be prepared by finely grinding the solid component a in the component b using a wet grinding mill such as a beads mill. It is also possible to prepare by finely grinding the solid component a with or without adding other components using a dry grinding mill such as a jet mill, and adding the thus obtained finely ground powder to the component b.

The solution in which a component a is dissolved in a component b can be prepared by dissolving the component a in the component b.

When the solid component a is dispersed (that is, suspended) in the component b in the form of fine particles, an average particle diameter of the fine particles is usually 15 µm or less, preferably 1 to 10 µm, and more preferably 1 to 5 µm.

When the composition of the present invention contains the component e, the first step includes the step of respectively suspending or dissolving the component a and the component e in the component b to prepare a suspension or a solution of the component a and the component e.

In the suspension or solution of the component a and the component e, the component a and the component e take any one of the following forms (1) to (4).

(1) Both the component a and the component e are suspended in the component b.
(2) The component e is dissolved in the component b, and the component a is suspended in the component b in which the component e has been dissolved.
(3) The component a is dissolved in the component b, and the component e is suspended in the component b in which the component a has been dissolved.
(4) Both the component a and the component e are dissolved in the component b.

The solid component a can take the form (1) or (2) depending on solubility of the solid component a in the component b and a weight ratio of the solid component a to the component b. When the component e is a component e which is solid at normal temperature (25° C.) (hereinafter sometimes referred to as a solid component e), the component e can take the form (1) or (3) depending on solubility of the solid component e to the component b and a weight ratio of the solid component e to the component b.

Suspensions of (1) to (3) can be prepared by the same operation as in a method for preparing the present suspension a. In the case of preparing the suspension (1), the solid component a and the solid component e may be finely milled at the same time by a wet grinding mill or a dry grinding mill, or the present suspension a and a suspension in which the solid component e has been suspended in the component b may be separately prepared, followed by mixing, in the method for preparing the present suspension a. In the case of preparing the suspension (2), usually, the component e is dissolved in the component b and then the solid component a is added to the solution. In the case of preparing the suspension (3), usually, the component a is dissolved in the component b and then the solid component e is added to the solution. The solution (4) can be prepared by dissolving the component a and the component e in the component b.

The second step of the present production method is the step of mixing the suspension or solution obtained in the first step with the aqueous solution of the component c to prepare liquid droplets.

In the aqueous solution of the component c used in the second step, the amount of the component c is usually from 0.5 to 30% by weight, and preferably from 1 to 20% by weight, based on the entire amount of the aqueous solution of the component c. To the aqueous solution of the component c, defoamers may be optionally added. The weight of the aqueous solution of the component c used in the second step is usually within a range of 0.8 to 2 times more than that of the suspension or solution obtained in the first step.

In the second step, the method for preparing liquid droplets in water includes, for example, a method in which the suspension or solution obtained in the first step is added to the aqueous solution of the component c, followed by stirring using a stirrer. The stirrer used in this case includes, for example, a propeller stirrer, a turbine stirrer, and a high-speed shear stirrer. Specific examples of the stirrer include T.K. Homo Mixer, T.K. Homomic Line Flow, T.K. Pipeline Homo Mixer, and T.K. Filmix manufactured by PRIMIX Corporation; CLEARMIX manufactured by M Technique Co., Ltd.; POLYTRON homogenizer and MEGATRON homogenizer manufactured by KINEMATICA AG; and SUPRATON manufactured by Tsukishima Kikai Co., Ltd.

An average particle diameter of liquid droplets existing in water obtained in the second step, that is, liquid droplets in the composition of the present invention, in which the component a is suspended or dissolved in the component b is usually from 5 to 60 μm, preferably from 10 to 60 μm, and more preferably from 10 to 40 μm.

In the present invention, the average particle diameter means a volume median diameter. The volume median diameter refers to a particle diameter at which a cumulative frequency in a volume equivalent frequency distribution is to be 50%, and the volume median diameter can be determined, for example, by wet measurement using a laser diffraction particle size distribution measuring apparatus. More specifically, liquid droplets are dispersed in water and then the volume median diameter is measured using the apparatus. The laser diffraction particle size distribution measuring apparatus includes, for example, Mastersizer 2000 (manufactured by Malvern Instruments Ltd.).

It is possible to obtain a pesticidal composition in the form of an aqueous emulsion in which liquid droplets in which the component a is suspended or dissolved in the component b are emulsified in an aqueous continuous phase, by the above production method. To the pesticidal composition in the form of an aqueous emulsion, the pesticide auxiliary agents and water may be further added.

The composition of the present invention can be applied to places such as paddy fields, cultivated lands, orchards, grass plot, and non-agricultural lands in the same manner as in the case of a conventional pesticidal composition in the form of an aqueous emulsion. The composition of the present invention is optionally diluted with water and then the obtained water dilution can be applied by a method in which the composition is applied to plants growing in the above places or the soil in the above places. Examples of the method for applying the water dilution include a soil surface application or foliage application method of the water dilution using a known sprinkler.

It is also possible to use the water dilution in a seed treatment, a seedling raising box treatment and the like.

The composition of the present invention can be applied as it is without being diluted with water and, for example, the composition of the present invention is applied along from levee to levee of paddy fields under flooding. Before application, the composition of the present invention is usually mixed by slightly shaking a vessel containing the composition of the present invention.

EXAMPLE

The present invention will be described in further detail below by way of Examples, but the present invention is not limited only to these Examples.

First, Preparation Examples and Comparative Preparation Examples are shown.

Preparation Example 1

2-[(2,5-dimethylphenoxy)methyl]-α-methoxy-N-methyl-benzeneacetamide (hereinafter referred to as a compound A) was dry-milled by a vertical type jet mill (JOM-0101-type jet mill, manufactured by Seishin Enterprise Co., Ltd.) to prepare compound A fine powders having an average particle diameter 10 μm or less. Ten (10) parts by weight of the obtained compound A fine powders were mixed with 20 parts by weight of liquid paraffin (manufactured by MORESCO Corporation under the trade name of MORESCO-WHITE P-40) to obtain a compound A suspension. Then, 30 parts by weight of the suspension was added to 33 parts by weight of an aqueous 5% by weight polyvinyl alcohol (manufactured by The Nippon Synthetic Chemical Industry Co., Ltd. under the trade name of GOHSENOL GH-17) solution. This mixture was stirred by a rotor-stator homogenizer (manufactured by KINEMATICA AG under the trade name of POLYTRON homogenizer) thereby emulsifying the compound A suspension in the aqueous polyvinyl alcohol solution to obtain a compound A emulsion.

To 14.2 parts by weight of deionized water, 0.4 part by weight of magnesium aluminum silicate (manufactured by Vanderbilt Company, Inc. under the trade name of VEEGUM Granules) was added, followed by stirring at room temperature for 15 minutes. To this solution, 0.2 part by weight of xanthan gum (manufactured by CP Kelco, Inc. under the trade name of KELZAN S) and 5 parts by weight of propylene glycol were added. This mixture was stirred at 60° C. for 60 minutes. The obtained dispersion was cooled to room temperature, and then 0.2 part by weight of an preservative (manufactured by Arch Chemicals, Inc. under the trade name of proxel GXL) was added to the dispersion to give a viscosity modifying liquid. Twenty (20) parts by weight of the viscosity modifying liquid, 17 parts by weight of water, and 63 parts by weight of the above compound A emulsion were mixed together to obtain the composition (1) of the present invention, containing 10% by weight of the compound A. Liquid droplets of the compound A suspension had an average particle diameter of 28.5 μm.

Preparation Example 2

By performing the same operation as in Preparation Example 1, except that the amount of the compound A fine powders prepared in Preparation Example 1 was changed from 10 parts to 5 parts by weight, and the amount of liquid paraffin (the same as mentioned above) was changed from 20 parts to 25 parts by weight, the composition (2) of the present invention, containing 5% by weight of the compound A was obtained. Liquid droplets of the compound A suspension had an average particle diameter of 25.7 μm.

Preparation Example 3

By performing the same operation as in Preparation Example 1, except that the amount of the compound A fine powders prepared in Preparation Example 1 was changed from 10 parts to 2.5 parts by weight, and the amount of liquid paraffin (the same as mentioned above) was changed to 27.5 parts by weight, the composition (3) of the present invention, containing 2.5% by weight of the compound A was obtained. Liquid droplets of the compound A suspension had an average particle diameter of 32.8 μm.

Preparation Example 4

By performing the same operation as in Preparation Example 1, except that the average particle diameter of liquid droplets of the compound A suspension was changed from 28.5 μm to 16.7 μm in the case of stirring using the rotor-stator homogenizer (the same as mentioned above), the composition (4) of the present invention, containing 10% by weight of the compound A was obtained.

Preparation Example 5

By performing the same operation as in Preparation Example 1, except that the average particle diameter of liquid droplets of the compound A suspension was changed from 28.5 μm to 7.7 μm in the case of stirring using the rotor-stator homogenizer (the same as mentioned above), the composition (5) of the present invention, containing 10% by weight of the compound A was obtained.

Next, Test Example will be shown.

Test Example 1

The compositions (1) to (5) of the present invention were respectively diluted with water so as to make each active ingredient concentration to 1,120 ppm. Each of the dilutions (100 μL) was added to a glass petri dish having a diameter of 6 cm, uniformly spread and then air-dried at room temperature. The petri dish was covered with a lid made of quartz glass and placed in a weathering tester (manufactured by Q-Lab Corporation under the trade name of Q-SUN Xenon Accelerated Weathering Tester, Model Xe-3) equipped with a borosilicate filter (manufactured by Q-Lab Corporation under the trade name of Daylight-BB Optical Filter) attached thereto, followed by irradiation with xenon light under the conditions of an intensity at 340 nm of 0.68 W/m$^2$ and a temperature of 34° C. (34° C. as measured by an insulated black panel thermometer) for 168 hours. After irradiation, the compound A remaining on the petri dish was extracted with acetonitrile, followed by quantitative analysis through high-performance liquid chromatography. A retention rate was determined by calculating as the weight percentage relative to the amount of the compound A before irradiation.

The results are shown in Table 1.

TABLE 1

| Composition used | Component b | Component a:Component b (weight ratio) | Average particle diameter (μm) | Retention rate (%) |
|---|---|---|---|---|
| Composition (1) of the present invention | Liquid paraffin | 33:67 | 28.5 | 57.3 |
| Composition (2) of the present invention | Liquid paraffin | 17:83 | 25.7 | 44.8 |
| Composition (3) of the present invention | Liquid paraffin | 8:92 | 32.8 | 25.7 |
| Composition (4) of the present invention | Liquid paraffin | 33:67 | 16.7 | 39.4 |
| Composition (5) of the present invention | Liquid paraffin | 33:67 | 7.7 | 33.0 |

The invention claimed is:

1. A pesticidal composition in the form of an aqueous emulsion, comprising:
    (a) an agriculturally active ingredient wherein said active ingredient is 2-[(2,5-dimethylphenoxy)methyl]-α-methoxy-N-methyl-benzeneacetamide;
    (b) a hydrophobic organic solvent;
    (c) a water-soluble polymer dispersing agent; and
    (d) water;
wherein liquid droplets in which the agriculturally active ingredient is suspended or dissolved in the hydrophobic organic solvent are emulsified in an aqueous continuous phase, and also a weight ratio of the agriculturally active ingredient to the hydrophobic organic solvent is from 5:95 to 70:30.

2. The pesticidal composition in the form of an aqueous emulsion according to claim 1, wherein the liquid droplets have an average particle diameter of 5 to 60 μm.

3. The pesticidal composition in the form of an aqueous emulsion according to claim 1, wherein the hydrophobic organic solvent is at least one hydrophobic organic solvent selected from the group consisting of esters, ketones, aromatic hydrocarbons, and paraffins.

4. The pesticidal composition in the form of an aqueous emulsion according to claim 1, wherein the water-soluble polymer dispersing agent is at least one water-soluble polymer dispersing agent selected from the group consisting of a vinyl-based polymer, polysaccharides, and derivatives thereof.

* * * * *